United States Patent [19]

de Paulis et al.

[11] Patent Number: 5,154,913

[45] Date of Patent: Oct. 13, 1992

[54] RADIOIODINATED BENZAMINES METHOD OF THEIR USE AS RADIOIMAGING AGENTS

[75] Inventors: Tomas de Paulis; Robert M. Kessler; Howard E. Smith, all of Nashville, Tenn.; Aaron Janowsky, Portland, Oreg.; Jeffrey A. Clanton, Nashville, Tenn.

[73] Assignee: Vanderbilt University, Nashville, Tenn.

[21] Appl. No.: 708,110

[22] Filed: May 28, 1991

Related U.S. Application Data

[63] Continuation of Ser. No. 604,370, Oct. 26, 1990, abandoned, which is a continuation of Ser. No. 122,390, Nov. 19, 1987, abandoned.

[51] Int. Cl.$^5$ .................. A61K 49/02; A61K 31/41
[52] U.S. Cl. ......................... 424/1.1; 514/359; 514/428; 548/567
[58] Field of Search .................. 424/1.1; 548/567; 514/359, 428

[56] References Cited

U.S. PATENT DOCUMENTS

| | | | |
|---|---|---|---|
| 3,342,826 | 9/1967 | Miller | 548/567 X |
| 3,591,634 | 7/1971 | Thominet | 548/567 X |
| 4,232,037 | 11/1980 | Florvall et al. | 548/567 X |
| 4,574,079 | 3/1986 | Gavras et al. | 424/1.1 |
| 4,673,686 | 6/1987 | Thominet et al. | 548/567 X |

FOREIGN PATENT DOCUMENTS

| | | | |
|---|---|---|---|
| 105599 | 4/1984 | European Pat. Off. | 548/567 |
| 130957 | 10/1980 | Japan | 548/567 |

OTHER PUBLICATIONS

Kung et al., "Preparation and Radiolabeling of IBZM," J. Lab CMPDS and Radio Pharm, vol. 23, Nos. 10–12, 1318–1319 (1986)–(Oct. 1986).

Crawley et al., "Dopamine Receptors in the Human Brain," Clin. Sci., 70:Supp 13, Abst 145 (Jan. 24, 1986).

Florvall et al, "Benzamide Derivatives," Eup Pat Appln 60,235, Mar. 1981, C.A. 27, 98:53687, vol. 98, 1983, p. 653.

Hall, et al, "Catechol Derivatives," E.P. 207,913, Jan. 1987, C.A. 106: 113551, vol. 106, 1987, p. 58.

Primary Examiner—Robert L. Stoll
Assistant Examiner—C. Sayala
Attorney, Agent, or Firm—Kenneth I. Kohn

[57] ABSTRACT

Novel, substituted benzamides in radioiodinated form are useful in radiopharmaceutical compositions in nuclear medicine as imaging agents to detect, visualize, and analyze the distribution and function of the dopamine D-2 receptor in the mammalian brain. The substituted benzamides and their racemic mixtures or their optically resolved enantiomers can be made by reacting a trialyltin substituted benzamide with an acid in the presence of radioactive iodine, generated by in situ oxidation of an appropriate iodide nuclide salt.

7 Claims, 1 Drawing Sheet

RADIOIODINATED BENZAMINES METHOD OF THEIR USE AS RADIOIMAGING AGENTS

This application is a continuation of application Ser. No. 604,370, filed Oct. 26, 1990 now abandoned, which is a continuation of Ser. No. 122,390, filed on Nov. 19, 1987 now abandoned.

FIELD OF THE INVENTION

The present invention relates to radiolabeled compounds, their method of making, and their method of use in clinical nuclear medicine. More specifically, the present invention relates to substituted benzamide which in radioiodinated form can be used in a radiopharmaceutical composition as an imaging agent, particularly for the brain. Some of the novel compounds of the present invention are described in co-pending application Ser. No. 122,382, which is incorporated herein for reference.

Radiolabeled compounds which are subject to localization in particular organs or tumors therein are of great value for diagnosis of diseases of the human body For example, thallium 201 and fatty acids labeled with carbon-11 and iodine-123 have been utilized as heart imaging agents. Also, various phosphonate ligands labeled with technetium-99m have been used to image infarcted regions of the heart. However, although many useful radiolabeled compounds are known, there remains a need for the discovery of improved compounds which are effective for routine imaging of the brain. In particular, there remains a need for radiolabeled compounds which are useful in imaging the dopamine D-2 receptor of the brain.

Butyrophenones and substituted benzamides labeled with iodine-125, iodine-123, and iodine-131 have been found to image dopamine receptors of the brain. However, previous agents lack the ability to selectively label only subpopulations of the dopamine D-2 receptors implicated in psychiatric disorders.

PRIOR ART

Japanese Patent Application 59112971 discloses an agent for detecting changes in dopamine receptors having the following structure:

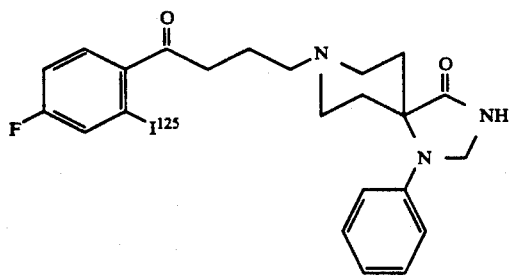

Landwater, S.W., *Label Comp. Radiopharm.* 22:273–278 (1985), disclosed the following compound which is described as a high affinity dopamine receptor probe:

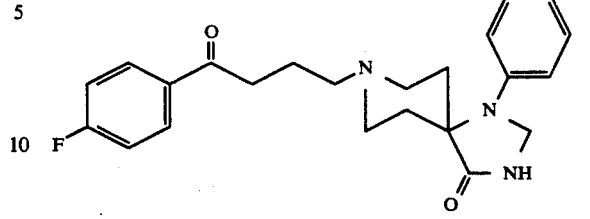

Crawley, F. C. W., et al., *Clin. Sci.* 70:Suppl. 13, Abstr. 145 (1986), and, independently, Kung, H. F., et al., *J. Label Comp. Radiopharm.* 23:1318–1319 (1986) discloses the following compound which is described as an agent for the studying of dopamine receptors in vivo:

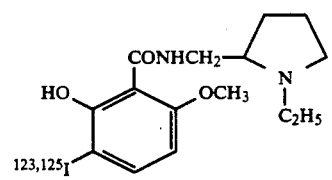

This compound, having a non-radioactive isotope of iodine, was disclosed in European Patent Application EP 60235.

European Patent Application EP 207913 discloses the following compound which is described as a brain dopamine receptor blocker:

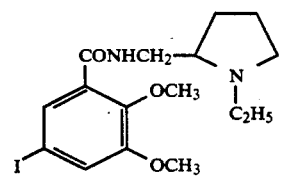

European Patent Application EP 156776 discloses the following compound which is described as a neuroleptic agent:

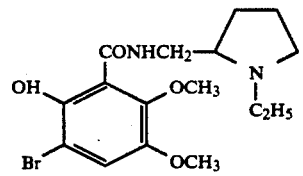

Neumeyer, J. L., et al., *J. Med. Chem.* 28:405–407 (1985), disclosed the following compound which is described to have receptor binding behaviour similar to that of haloperidol:

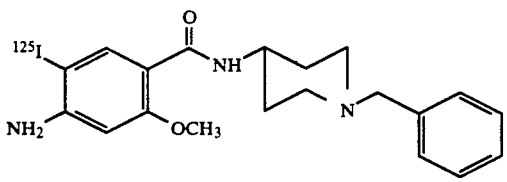

Wilson, A. A., et al., *J. Nucl. Med.* 28:729 (1987), disclosed the following compound which is described to bind to brain receptors blockable by haloperidol:

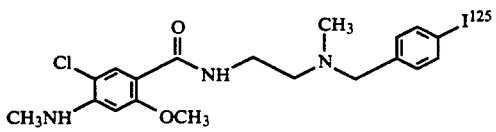

Martres, M. -P., et al., *Eur. J. Pharmacol.* 118:211-219 (1985), disclosed the following compound which is described as a selective ligand for dopamine D-2 receptors:

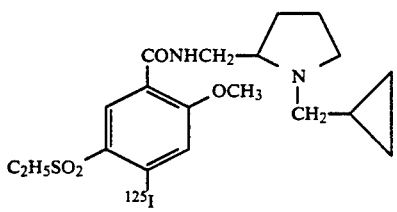

The compounds of this invention, labeled with iodine-125, iodine-123 and iodine-131 have been found to possess the properties which predict these agents to have superior qualities in this respect. The radioiodinated substituted benzamides are easily synthesized from a suitable precursor, i.e., a trialkyltin derivative or a triazene derivative of the corresponding substituted benzamide.

SUMMARY OF THE INVENTION

Figure 1:
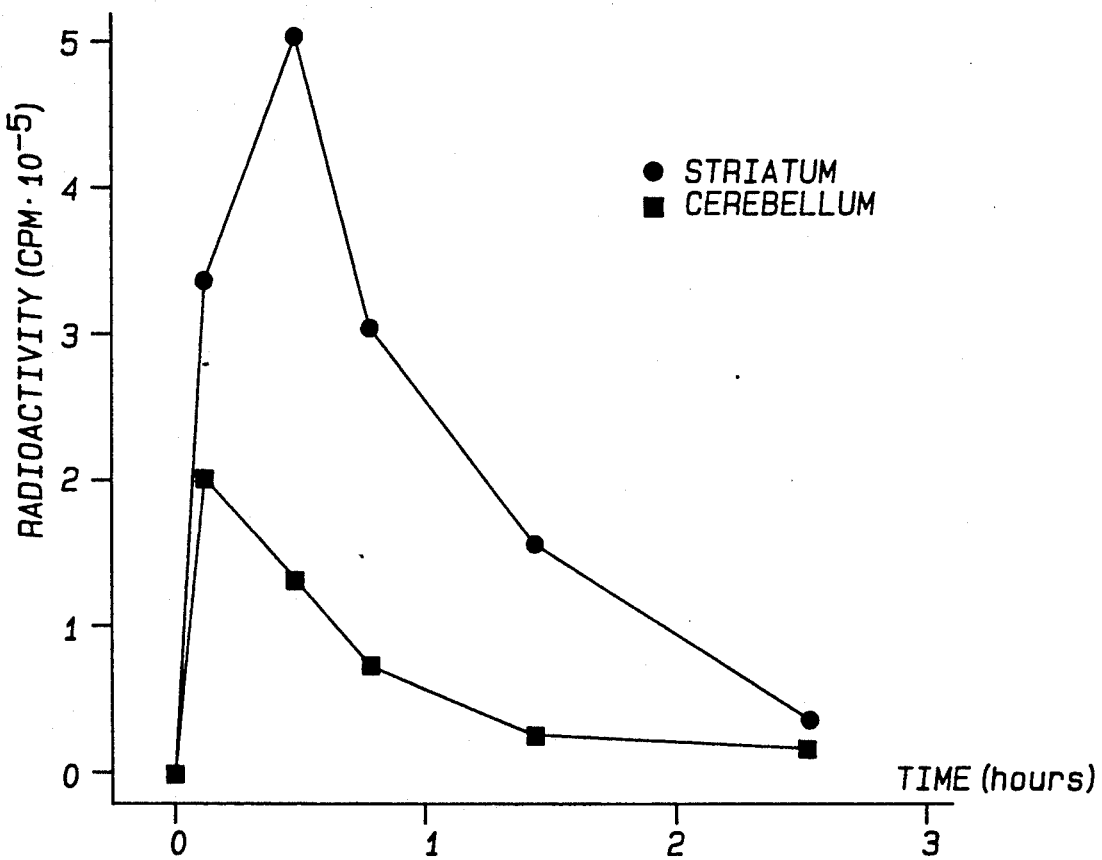
FIG. 1 is a graphic representation of in vivo binding studies of the radioiodinated substituted benzamine of the present invention demonstrating its properties of having rapid penetration into the rat brain and labeling of the dopamine D-2 receptor.

The present invention relates to novel radiopharmaceutical substituted benzamides. In addition, the present invention relates to a method of making the novel radioiodinated compound as well as to radiopharmaceutical compositions comprising the compound and their method of use as diagnostic compositions. The advantage of using the compounds of the present invention over those of the prior art is a) their facile preparation and radioiodination, b) the utilization of both enantiomers for enhanced image contrast, and c) their selective binding to a hypothetical subpopulation of dopamine D-2 receptors in the brain thought to be involved in psychiatric disorders. A radiopharmaceutical composition of the present invention comprises radioiodinated substituted benzamide and a pharmaceutical carrier such as physiological buffered saline solution. A method for diagnostic imaging comprises the steps of systematically applying to humans an effective amount of a radiopharmaceutical composition comprising radioiodinated substituted benzamides and subsequently making an image by detecting gamma radiation emitted by said radiological composition following its localization on dopamine D-2 receptors in the target organ.

DESCRIPTION OF THE INVENTION

Various substituted benzamides which undergo the radioiodination reaction of the present invention are either known compounds or can be formulated by the procedures described in copending application Ser. No. 122,388, filed Nov. 19, 1987, incorporated herein for references. Briefly, these benzamides can be obtained by reacting a halogen substituted benzamide with bis(trialkyltin) in the presence of a palladium catalyst. For example, substituted benzamide derivatives represented by the formula:

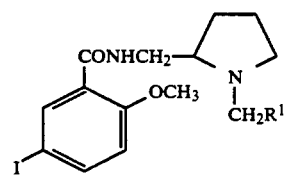

wherein $R^1$ is a hydrogen atom, a lower alkyl group consisting of 1 to 4 carbon atoms, a cycloalkyl group consisting of 3 to 7 carbon atoms, an alkenyl group consisting of 2 to 4 carbon atoms, an alkynyl group consisting of 2 to 4 carbon atoms, a phenyl group, a halogen-substituted phenyl group, or an enantiomer or pharmaceutically suitable salt thereof may be obtained by the reaction of the intermediate compound:

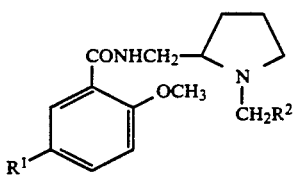

wherein $R^1$ is tributyltin group with a radioactive isotope of iodine in a protic solvent such as ethanol or hydrochloric acid. The iodine can be generated in situ by decomposition of iodine monochloride or by oxidation of the alkali metal iodide with hydrogen peroxide or an agent such as the sodium salt of N-chloro-p-toluenesulfonamide.

Further, compounds of the preferred formula can be obtained by reaction of the intermediate compound, wherein $R^1$ is a triazeno group of the formula:

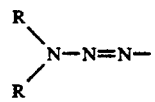

wherein R is a lower alkyl group of 1 to 4 carbon atoms or constitutes a 5- or 6-member ring, which is reacted with an acid, such as hydrochloric acid or trifluoroacetic acid, in the presence of iodide in the solvent, such as acetone, formic acid, or acetonitrile.

It has been discovered that when substituted benzamides are radioiodinated they are useful radiopharmaceuticals for imaging the dopamine D-2 receptor in the brain and therefore are useful in brain imaging experiments.

In vitro receptor binding studies of the radioiodinated substituted benzamides have shown them to be selective antagonists of central dopamine D-2 receptors. A compound of this invention (Example 1) could be competitively displaced to 50% at 1–2 nM inhibitory concentration by haloperidol or at 1.3 nM inhibitory concentration by raclopride from their binding sites in rat brain homogenates.

In vivo receptor binding studies of the radioiodinated substituted benzamides have shown a rapid penetration into the rat brain (FIG. 1). Peak uptake in the striatum was observed after 20 minutes. After 60 minutes, the ratio of radioactivity in the striatum was 7.3 times higher than that in the cerebellum, showing a preferential binding to dopamine-rich structures of the brain. Pretreatment of haloperidol reduced the uptake of the radioiodinated benzamide in striatum to 23% of that of untreated rats.

Radioiodinated substituted benzamide compounds suitable for use herein can be synthesized by the Sandmeyer reaction to introduce the radioligand. The intermediate diazonium derivative is generated by acid decomposition of the corresponding pyrrolidinotriaze. The benzamide compounds of this invention can also be obtained by acid-catalyzed iododestannylation of the corresponding trialkyltin derivatives. The radioiodination technique is illustrated in the examples. I-123, I-125, and I-131 radioligands are preferably employed as imaging agents for the brain. A pharmaceutical composition of the present invention comprises one of the aforementioned isotopes of radioiodinated substituted benzamides and a carrier such as physiological buffered saline solution. It is contemplated that the composition will be systematically administered to the patient as by intravenous injection. Suitable dosages for use as a diagnostic imaging agent are from about 2 to about 20 mCi of I-123 labelled iodobenzamides for D-2 dopamine receptors, that is, as imaging agents for the brain. It will be appreciated by those skilled in the art that the novel imaging agent of the present invention is employed in accordance with conventional methodology in nuclear medicine in a manner analogous to functional brain imaging. Thus, a composition of the present invention is systematically applied to the patient and subsequently the uptake of the composition in the selected organ is measured and an image formed, for example, by means of a conventional gamma radiation CT camera.

Further understanding and use of the present invention can be obtained from the examples and from Budinger, T. F., Physical Attributes of Single-Photon Tomography, *J. Nucl. Med.* 21:579–592 (1980).

In the process of preparing the radiolabelled substituted benzamides of the present invention, the radioactive iodine atom is introduced in the last step of the synthesis. In this manner, the radiation hazard will be limited in the preparation and purification of the ligands.

The compounds of the present invention are characterized by the Formula I:

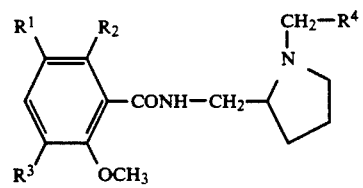

wherein $R^1$ is $^{123}I$, $^{125}I$, $^{131}I$, $R^2$ is a hydrogen atom or a hydroxyl group, $R^3$ is a hydrogen atom, a halogen atom, a hydroxyl group, or a methoxy group, $R_4$ is an alkyl group of 1 to 4 carbon atoms, an alkenyl group of 2 to 4 carbon atoms, an alkynyl group of 2 to 4 carbon atoms, a cycloalkyl group of 3 to 6 carbon atoms, or a halogen-substituted phenyl group, or an enantiomer thereof.

Preferred compounds of the present invention are:

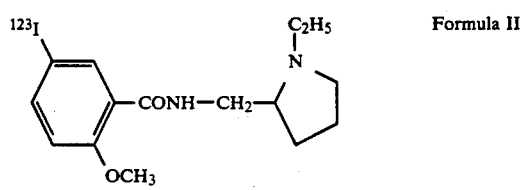

Formula II

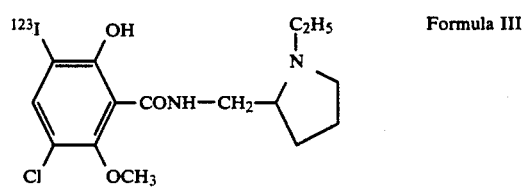

Formula III

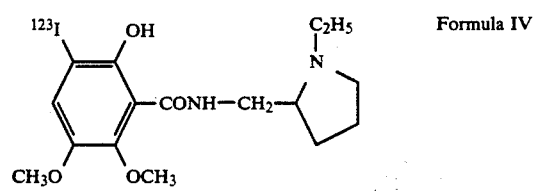

Formula IV

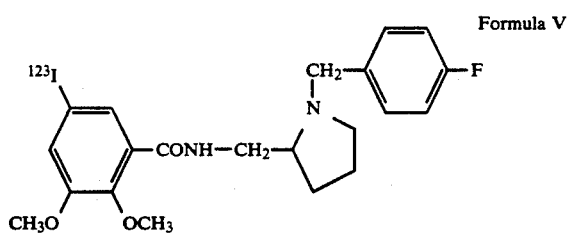

Formula V

The above-noted compounds are used to detect, visualize and analyze the distribution and function of the dopamine D-2 receptor in the mammalian brain as racemic mixtures or as their optically resolved anantiomers. The corresponding enantiomers can be obtained by using the optical stereoisomers of the appropriate synthetic precursor.

Suitable iodine isotopes for single photon (gamma) auto radiography or computed tomography are iodine-123 for maximum specific radioactivity at $9 \times 10^6$ Ci/mmol, iodine-125 for $2 \times 10^3$ Ci/mmol, and iodine-131 for $1.6 \times 10^4$ Ci/mmol.

Compounds of the present invention can be obtained by one of the following methods of synthesis.

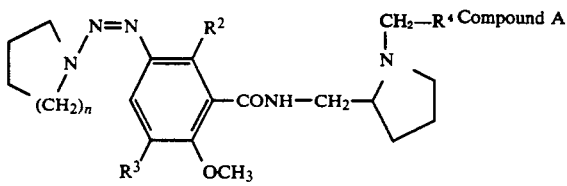

Compounds of Formula A wherein n=1 or 2, $R^2$ is a hydrogen atom or a hydroxyl group, $R^3$ is a hydrogen atom, a halogen atom, a hydroxyl or methoxyl group and $R^4$ is an alkyl of 1 to 4 carbon atoms, an alkenyl group of 2 to 4 carbon atoms or an alkynyl group of 2 to 4 carbon atoms, a phenyl group, or a para-halogen-substituted phenyl group, are treated with an organic acid such as trifluoroacetic acid or an inorganic acid such as hydrochloric acid in the presence of radioactive sodium or potassium iodide in an aprotic solvent such as acetone, benzene, or acetonitrile.

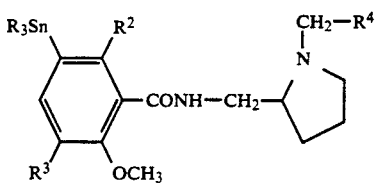

Compounds of Formula B wherein R is an alkyl of 1 to 5 carbon atoms such as n-butyl, $R^2$, $R^3$ and $R^4$ are defined as before are treated with radioactive iodine in a protic solvent such as ethanol or dilute hydrochloric acid. The iodine can be generated in situ by oxidation of sodium iodide with hydrogen peroxide or chloramine-T, or by using radioactive iodine monochloride.

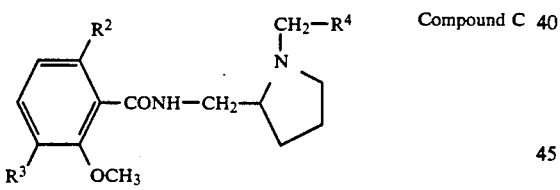

Compounds of Formula C wherein $R^2$, $R^3$ and $R^4$ are defined as in Formula I are treated with radioactive iodine in a solvent such as chloroform or dioxane at elevated temperature.

The following examples describe in detail compounds illustrative of the present invention and methods which have been devised for their preparation.

EXAMPLE 1

[$^{125}$I](S)-N-[(1-Ethyl-2-pyrrolidinyl)methyl-5-iodo-2-methoxybenzamide

A solution of (S)-N-[1-ethyl-2-pyrrolidinyl)methyl]-2-methoxy-5-[3,3-(1,4-butanediyl)]triazenebenzamide (1.5 μg, 4.7 nmol) in benzene (9 μl) was mixed with 1.8 mCi of Na$^{125}$I (0.5 μg, 520 nmol in formic acid (10 μl) was added and the reaction mixture was shaken for 40 min. at 20° C. Aqueous 1N NaOH (300 μl) was added. Extraction with benzene (2×100 μl) gave the iodine substituted benzamide. Extraction of the combined organic layer with 0.1N HCl (2×150 μl) gave 0.41 mCi of pure product. Specific activity 560 Ci/mmol, radiochemical yield 22%.

EXAMPLE 2

[$^{125}$I](R)-N-[(1-Ethyl-2-pyrrolidinyl)-5-iodo-2-methoxybenzamide

A solution of (R)-N-[(1-ethyl-2-pyrrolidinyl)methyl[-2-methoxy-5-tri-n-butyltinbenzamide (15 μg, 22 nmol) in diethylether (10 μL) was mixed with 10.4 mCi of Na$^{125}$I (3.2 μg, 22 nmol) in 0.001N NaOH (29 μL). Hydrochloric acid (0.1N, 10 μL) was added followed by the addition of an aqueous solution (5 μL) of sodium N-chloro-4-methylbenzene sulfonamide (16 μg, 70 nmol). After 10 min. at 20° C., NaOH (2N, 20 μL) was added. Extraction with ether (2×150 μL) gave 7.2 mCi of the desired iodobenzamide. Specific activity 590 Ci/mmol, radiochemical yield 70%.

EXAMPLE 3

[$^{125}$I](S)-5-Chloro-N-[1-ethyl-2-pyrrolidinyl)-methyl]-3-iodo-6-methoxysalicylamide A solution of (S)-5-chloro-N-[(1-ethyl-2-pyrrolidinyl) methyl]-6-methoxysalicylamide (de Paulis, T., et al., J. Med. Chem., 28:1263-1269 (1985)(9.4 μg, 30 nmol) in ethanol (30 μL) was mixed with a solution of 10 mCi of Na$^{125}$I (4.5 μg, 330 Ci/mmol, 30 nmol) in 0.001N NaOH (30 μL). A solution of chloramine-T (13 μg, 50 nmol) in water (10 μL) was added. The mixture was heated to 60° C. for 45 min. Addition of 0.1N NH$_4$Cl (100 μL) and extraction with ether (2×150 mL) gave 7.6 mCi of product. Extraction of the combined organic layer with 0.1N HCl (3×100 μl ) gave 4.6 mCi of pure iodine substituted benzamide (specific activity 330 Ci/mmol). Thin layer chromatography (SiO$_2$, Merck F$_{254}$) in isopropylethermethanol-conc. NH$_{4-OH}$ (160:39:1) showed radioactivity at Rf 0.16, identical to that of an authentic sample. (The starting material had Rf 0.26). Radiochemical yield 46%.

EXAMPLE 4

[$^{125}$I](S)-N-](S)-N-[1-Ethyl-2-pyrrolidinyl)methyl-3-iodo-5,6-dimethoxysalicylamide A solution of (S)-N-[(1-ethyl-2-pyrrolidinyl)methyl]-5,6-dimethoxysalicylamide (Eur. Pat. Appl. EP 156 776)(6.8 μg, 22 nmol) in ethanol (20 μL) was added to 6.13 mCi of Na$^{125}$I (3.2 μg, 22 nmol) in 0.001N NaOH (20 μL). A solution of chloramine-T (10 μg, 44 nmol) in water (7 μl) was added at 20° C. After 15 min 1N NH$_4$Cl (50 μL) and 2N NH$_4$OH (20 μL) were added. Extraction with ether (3×150 μL) combining of the organic layer and extracting with 0.1N HCl (2×100 μl) gave pure iodobenzamide (specific activity 220 Ci/mmol and radiochemical yield 72%). Thin layer chromatography showed radioactivity at Rf 0.36, identical to that of an authentic sample. The starting material had Rf 0.42.

EXAMPLE 5

[$^{125}$I](R)-N-[(1(4-Fluorobenzyl)-2-pyrrolidinyl)methyl]-5-iodo-2-methoxybenzamide A solution of (R)-N-[(1-(4-fluorobenzyl)-2-pyrrolidinyl)methyl]-5-iodo-2-methoxybenzamide hydrochloride hydrate (0.52 g, 1.0 mmol) in triethylamine (30 ml) was treated with palladium(II) acetate (20 mg, 0.10 mmol), tetrakis(triphenylphosphine) palladium(0) (60 mg, 0.05 mmol), and bis(tributyltin)(0.61 g, 1.05 mmol)

at 85° C. for 3 h. Filtration and washing of the isoluble material with triethylamine (10 mL), followed by evaporation of the solvent gave 1.1 g of a yellow oil. Separation on silica gel with a gradient of hexane-isopropylether-ethyl acetate-ethanol gave fractions with the corresponding tributyltinbenzamide as an oil. A 2N solution of this oil in ether was prepared. 1 mCi of Na$^{125}$I (specific activity 200 Ci/mmol, 45 nmol) was prepared in 0.1N HCl(10 μL, 1 μmol) and added to the benzamide solution (25 μL, 50 nmol). An aqueous solution of chloramine-T (10 μL, 149 nmol) was added. After 30 min. the reaction mixture was neutralized with an excess of 2N NaOH (20 μL, 40 μmol) and the product was extracted with ether (3×150 μL). TLC showed radioactivity at Rf 0.57 identical to that of the starting iodobenzamide.

EXAMPLE 6 (Intermediates)

(S)-(−)-N-[(1-Ethyl-2-pyrrolidinyl)methyl]-5,6-dimethoxy-3-tributyltinsalicylamide To a solution of (S)-(−)-N-[(1-ethyl-2-pyrrolidinyl)-methyl]-2-bromo-5,6-dimethoxysalicylamide (GB 2153354) (0.42 g, 1.0 mmol) in triethylamine (30 mL, freshly distilled from calcium hydride) was added palladium(II) acetate (20 mg, 0.1 mmol), tetrakis(triphenyl-phosphine)palladium(0), (60 mg, 0.05 mmol) and bis(-tributyltin) 0.85 g (1.4 mmol) under nitrogen atmosphere at 25° C. The mixture was heated to reflux (85° C.) for 16 h. The solvent was evaporated and the residue was subjected to column chromatography on silica el (Merck, 0.063–0.200 mm) with hexeneethyl acetate (10:1) as eluent. Fractions with a single spot on TLC with Rf 0.58 in isopropylethermethanol-conc. ammonium hydroxide (160:39:1) were collected and the solvent was removed by evaporation. This gave 0.30 g (50%) of an oil. NMR of low field regions: δ 7.08 (s, 1H), 3.93 (s, 3H) and 3.84 ppm (s, 3H). Part of the butyl signal appears at 0.89 ppm.

By the same method, the following organotin-benzamides were prepared from their corresponding bromo or iodo derivatives:

(S)-(−)-N-[(1-Ethyl-2-pyrrolidinyl)methyl]-2-methoxy-5-tributyltinbenzamide TLC: Rf 0.32 (i-Pr$_2$O-MeOH-NH$_3$, 160:39:1) from the iodo-derivative (Rf 0.12) NMR: δ 8.26 ppm (d, J=3 Hz, C(6)-H).

(S)-(−)-N-[(1-Ethyl-2-pyrrolidinyl)methyl]-6-methoxy-3-tributyltinsalicylamide. TLC: Rf 0.43 (i-Pr$_2$O-MeOH-NH$_3$, 160:39:1), from the bromo derivative (Rf 0.35), NMR: δ 7.33 ppm (d, J=10 Hz, C(4)H).

(R)-(+)-N-[(1-(4-Fluorobenzyl)-2-pyrrolidinyl)methyl]-2,3-methoxy-5-tributyltinbenzamide, TLC: Rf 0.61 (i-Pr$_2$O-MeOH-NH$_3$, 160:39:1), from the iodo derivative (Rf 0.58), NMR δ 8.32 ppm (d, J=2.6 Hz, C(6)-H)

(S)-(−)-N-[(1-Ethyl-2-pyrrolidinyl)methyl]-2,3-dimethoxy-3-tributyltinbenzamide. TLC: Rf 0.56 (i-Pr$_2$O-MeOH-NH$_3$, 160:39:1), from the iodo derivative (Rf 0.53), NMR δ 7.77 (d, J=1.2 Hz) and 7.11 ppm (d, C(4)-H).

EXAMPLE 7

Sulpiride, a neuroleptic agent, has a high selectivity in blocking the D-2 receptor, see Fuxe, K. et al., *Neurosci. Lett.* 64:163–168 (1986). Its radioligand [$^3$H]sulpiride, was compared to ]$^{125}$I](S)-N-[(1-ethyl-2-pyrrolidinyl)methyl]-5-iodo-2-methoxybenzamide ([$^{125}$I](S)-II in a receptor binding assay.

Male Sprague-Dawley rats (150–200 g) were killed by decapitation and their brains quickly removed and dissected on ice. Striata were dissected and homogenized in 40 vol of ice-cold Tris-HCl (50 mM) containing 123 mM NaCl, 5 mM KCl, 2 mM CaCl$_2$ and 1 mM MgCl$_2$ (pH 7.4) using a Brinkman Polytron. The suspension was centrifuged at 30,000×g for 10 min. at 4° C., and the pellet was resuspended in 40 vol. of fresh buffer with polytron. The suspension was incubated at 37° C. for 10 min, centrifuged again at 30,000×g for 10 min. (4° C.) and the final pellet was resuspended with the polytron in 200 vol of ice cold buffer. Assay tubes contained 50 μM or radioligand at 2.9 nM concentration and 90 μL of the striatal membrane preparation. Nonspecific binding was determined in the presence of 10 μM(−)[$^{125}$I](S)-II. Tubes were incubated for 30 min. at 37° C., poured over Whatman GF/B filters under vacuum, and the filters were rinsed three times with 4 mL of ice cold buffer. Radioactivity remaining on the filters was measured by liquid scintillation on a Quantum 9 Multichannel analyzer operating at 35% efficiency. Results are shown in Table I.

TABLE I

| Compound$^a$ | [$^{125}$I]-(S) II binding$^b$ IC$_{50}$ (nM) | [$^3$H]sulpiride$^c$ binding IC$_{50}$ (nM) |
|---|---|---|
| (R)-II | 169 | 146 |
| (S)-II | 5.0 | 3.6 |
| Sulpiride | 45 | 28 |

$^a$)Each compound was dissolved in 0.2 mL of HOAc and diluted with buffer.
$^b$)Radioligand concentration 0.46 nM. Nonspecific binding was determined in the presence of 10 μM of (S)-II.
$^c$)Radioligand concentration 2.9 nM. Nonspecific binding was determined in the presence of 10 μM sulpiride.

The binding of [$^{125}$I](S)-II to rat striated membranes was saturable, reversible and stereospecific under the conditions described above. Binding reached equilibrium at 37° C. within 20 min., and remained stable for at least 60 min. Scatchard anlysis of the saturation isotherm revealed a single set of binding sites with a K$_d$ of 1.0 nM and a maximal number of binding sites of 169 fmol/mg protein. Sulpiride displaced the radioligand with an IC$_{50}$ of approximately 45 nM. In a displacement experiment using [$^3$H](S)-(−)-sulpiride as the radioligand, the two enantiomers (R)-II and (S)-II had IC$_{50}$ values of 146 nM and 3.6 nM, respectively (RS)-sulpiride had IC$_{50}$ 28 nM.

It will be readily apparent that one skilled in the art having benefit of the foregoing disclosure of the present invention may make modifications or variations of the invention without departing from the spirit thereof. Therefore, it is intended that the scope of the present invention be limited by the spirit and contents of the appended claims.

What is claimed is:

1. [$^{123}$I](S)-N-[(1-ethyl-2-pyrrolidinylmethyl]-5-iodo-2-methoxybenzamide.

2. [$^{123}$I](R)-N-[(1-4fluorobenzyl-2-pyrrolidinyl)methyl]-5-iodo-2-methoxybenzamide.

3. [$^{123}$I](S)-N-[1-ethyl-2-pyrrolidinyl)methyl]-5-chloro-3-iodo-6-methoxysalicylamide.

4. [$^{123}$I](R)-N-[1-(4-fluorobenzyl)-2-pyrrolidinyl)methyl]5-iodo-2,3-dimethoxybenzamide.

5. [$^{123}$I](S)-N-[(1-ethyl-2-pyrrolidinyl)methyl]-5-iodo-2,3-dimethoxybenzamide.

6. [$^{123}$I](S)-N-[(1-ethyl-2-pyrrolidinyl)methyl]-3-iodo-5,6-dimethoxysalicylamide.

7. A method of radioimaging a human brain comprising the steps of:
(a) systematically applying a radioiodinated substituted benzamine selected from the group consisting of [$^{123}$I](S)-N-[(1-ethyl-2-pyrrolidinylmethyl]-5-iodo-2-methoxy-benzamide; ($^{123}$I)(R)-N-[1-ethyl-2-pyrrolidinyl)methyl]-5-iodo-2-methoxy-benzamide; [$^{123}$I](S)-5-chloro-N-[1-ethyl-2-pyrrolidinyl)-methyl]-3-iodo-6-methoxysalicylamide; [$^{123}$I](R)-N-[(1-(4-fluorophenyl-2-pyrrolidinyl)methyl]-5-iodo-2-methoxybenzamide; and [$^{123}$I](S)-N-[(1-ethyl-2-pyrrolidinyl)methyl]-3-iodo-5,6-dimethoxysalicylamide; [$^{123}$I](R)-N-[(1-ethyl-w-pyrrolidinyl)methyl]-5-iodo-2,3-dimethoxy-benzamide.

* * * * *